United States Patent [19]

Frank et al.

[11] Patent Number: 5,686,309
[45] Date of Patent: Nov. 11, 1997

[54] METHOD AND APPARATUS FOR DETERMINATION OF HEMOGLOBIN CONTENT OF INDIVIDUAL RED BLOOD CELLS

[75] Inventors: Robert Stewart Frank, Pembroke Pines; James Lynn Wyatt, Plantation, both of Fla.

[73] Assignee: Coulter International Corp., Miami, Fla.

[21] Appl. No.: 588,793

[22] Filed: Jan. 19, 1996

[51] Int. Cl.$^6$ .................................................. G01N 33/72
[52] U.S. Cl. .................... 436/66; 436/63; 436/149; 436/150; 422/73; 422/82.01; 422/82.02; 435/2; 324/71.1
[58] Field of Search .................. 436/63, 66, 149, 436/150, 151; 324/71.1; 422/73, 82.01, 82.02; 435/2

[56] References Cited

U.S. PATENT DOCUMENTS

| | | | |
|---|---|---|---|
| 2,656,508 | 10/1953 | Coulter | 324/71.1 |
| 3,502,974 | 3/1970 | Coulter et al. | 324/71.1 |
| 3,836,849 | 9/1974 | Coulter | 324/71.1 |
| 4,052,596 | 10/1977 | Vick | 377/10 |
| 4,298,836 | 11/1981 | Groves et al. | 324/71.1 |
| 4,735,504 | 4/1988 | Tycko | 356/336 |
| 4,876,205 | 10/1989 | Green et al. | 436/66 |
| 5,125,737 | 6/1992 | Rodriquez et al. | 356/39 |
| 5,149,503 | 9/1992 | Kohno et al. | 422/82.05 |
| 5,194,909 | 3/1993 | Tycko | 356/40 |
| 5,583,432 | 12/1996 | Barnes | 324/204 |

OTHER PUBLICATIONS

Clark, et al. "Study on the Dehydrating Effect of the Red Cell . . . Water Contents," Biochimica et Biophysica Acta, 646:422–432 (1981).

Schwan, H.P., "Electrical Properties of Blood and its Constituents: Alternating Current Spectroscopy," Blut, 46:185–197 (1983).

Leif, R.C., et al, "Two–Dimensional Impedance Studies of BSA Buoyant Density Separated Human Erythrocytes," Cytometry, 6:13–21 (1985).

Pilwat, G., et al., "Determination of Intracellular Conductivity from Electrical Breakdown Measurements," Biochimica of Biophysical Acta, 820:305–314 (1985).

Primary Examiner—Maureen M. Wallenhorst
Attorney, Agent, or Firm—Mitchell E. Alter

[57] ABSTRACT

This invention is related to an apparatus and method to determine the hemoglobin concentration of individual red blood cells by measuring the radio frequency resistance (RF) and direct current (DC) resistance resulting during the flow of the cells through a measurement aperture. The hemoglobin concentration of the cell is determined using the ratio of these two resistances. This determination can be made using a focused flow cell and a non-focused flow cell. In addition, the determination can be made with red blood cells which are either in their native, deformable state or with red blood cells that have been isovolumetrically sphered.

20 Claims, 7 Drawing Sheets

METHOD AND APPARATUS FOR DETERMINATION OF HEMOGLOBIN CONTENT OF INDIVIDUAL RED BLOOD CELLS

FIELD OF THE INVENTION

The present invention relates to the measurement of the hemoglobin concentration of individual red blood cells in a whole blood sample. More specifically, the present invention relates a method for making such measurement and for determining statistical characteristics and identifying subpopulations of the sample.

BACKGROUND OF THE INVENTION

The evaluation of the properties of an individual's red blood cells is a standard part of the evaluation of the health of the individual and is used in the diagnosis of certain diseases and the monitoring of treatments. Properties of the red blood cell that are routinely reported include the number of red cells per unit volume of blood (called the "Red Cell Count" or "RBC"), the volume percentage of red cells in whole blood (Packed Cell Volume or PCV), the amount of hemoglobin per unit volume of whole blood (Hemoglobin Concentration or [Hgb]), the average size of the red cell (Mean Cell Volume or MCV) and the distribution of red cell sizes (Red Cell Distribution Width or RDW), the average amount of hemoglobin in each red blood cell (Mean Cell Hemoglobin or MCH) and the average concentration of hemoglobin within the red blood cell (Mean Cell Hemoglobin Concentration or MCHC). Of these reported parameters, most hematology analyzers directly measure only three: Red Cell Count (RBC), Hemoglobin Concentration ([Hgb]), and Mean Cell Volume (MCV). The other parameters are calculated according to the following relationships.

1. $PCV = RBC \times MCV$

2. $MCH = [Hgb]/RBC$

3. $MCHC = [Hgb]/PCV$

4. $RDW = \text{Standard Deviation of Volume}/MCV$

The reported red cell parameters are used to describe the status of a patient's blood sample and relate to the classification and diagnosis of anemia. For example, subclassification of anemias is possible using the MCV. Decreased MCV is seen in the microcytic anemias such as iron deficiency or thalassemia. Increased MCV occurs with the macrocytic anemias of B12/folate deficiency or aplastic anemia. Normocytic anemias (normal MCV) include immune hemolytic anemia or hereditary spherocytosis. Narrowing of the classification is possible with the addition of other parameters, such as MCHC or MCH. For the microcytic anemias, iron deficiency shows a decrease in both MCV and MCHC, whereas only MCV is decreased in thalassemia. In addition, the distribution of values within the red blood cell population adds increased information. For example, with microcytic anemias, the RDW is increased for iron deficiency but not for thalassemia.

Other analytical factors are useful in fully assessing a particular patient's blood sample and potentially allow for early diagnosis and treatment of diseases. Analysis of the distribution of the individual cell hemoglobin concentration within a population adds significant information concerning the flow properties of red cells. The distribution of the individual red cell hemoglobin concentration is roughly equivalent to the manual assessment on a microscope slide of the color of the cells. Red cells with decreased hemoglobin concentration are called hypochromic, while red cells with increased hemoglobin concentration are termed hyperchromic. Populations with an increased distribution of hemoglobin concentration are classified as polychromatophilic. Hyperohromic red cells have altered flow properties and have been suggested as the cellular cause of the hemolytic crisis in diseases such as sickle cell anemia.

In their current form, there are several problems and limitations associated with the measurements of mean cell hemoglobin and mean cell hemoglobin concentration. First, these measurements are usually made as an average measurement for the entire cell population. Thus it is impossible to obtain the distribution of these measurements within the population or to identify multiple populations or subpopulations. Secondly, since the measurements of mean cell hemoglobin and mean cell hemoglobin concentration are not determined directly, but rather calculated from two or more measurements as described in the equations above, a potential for error exists due to these multiple measurements.

In the reference method, MCHC is determined by dividing the hemoglobin content by the packed cell volume. In the case of automated hematology analyzers, packed cell volume is not determined directly, but is determined as the cell count times the mean cell volume. On many automated systems there is a known inaccuracy in the volume measurement for samples with abnormal hemoglobin concentration. Thus, this error in volume propagates into the measurement of mean cell hemoglobin concentration.

Automated means to make electrical resistance or optical measurements on individual blood cells as they pass substantially one cell at a time through an aperture is well known in the art of cytometry. The seminal patent (Wallace H. Coulter, U.S. Pat. No. 2,656,508, October 1953), describes a method to measure the direct current (DC) resistance of individual cells as they pass through an aperture. The relationship of this low frequency measurement to the volume and shape of the cell has subsequently been well described. In the patent by Coulter and Hogg (U.S. Pat. No. 3,502,974, March 1970) the measurement of the radio frequency resistance of cells during passage through such an aperture is taught. It is equally well known that the RF resistance measurement is influenced by the size, shape, and internal conductivity of the cell. By determining the ratio of the RF resistance to the DC resistance, a ratio referred to as the "opacity" of the cell, one can eliminate the influence of the size of the cell and create a measure that is only dependent on the internal conductivity of the cell and its shape. The opacity measurement has been used in several applications to differentiate subpopulations of blood cells within a larger population, such as for the identification of specific white cell types or for the differentiation of platelets from red cells. This differentiation is based on the relative measure of one population versus another and does not involve the quantification of the specific cellular properties responsible for the observed measurement.

Leif et. al., "Two-dimensional Impedance Studies of BSA Buoyant Density Separated Human Erythrocytes," *Cytometry*, 6:13–21, 1985, described the use of the opacity measurement to distinguish between red cells of varying density. However, they did not recognize the use of the opacity measurement for the determination of the hemoglobin concentration of the cell. The quantification of the hemoglobin concentration of individual red cells using the opacity measurement has not been previously described or practiced.

The use of electrical means to interrogate the properties of specific components of blood and other cells has been practiced since the beginning of the 20th century. The study of the electrical properties of blood and other biological fluids by making a series of measurements at different frequencies has been termed "alternating current spectroscopy". A review of this literature is given by Schwan, "Electrical Properties of Blood and Its Constituents: Alternating Current Spectroscopy," *Blut*, 46:185–197, 1983. Numerous investigators have studied the resistive and dielectric properties of whole blood over a range of frequencies from DC to the microwave. It was recognized early in this period that the electrical conductivity of whole blood was different for low frequency electrical currents and RF electrical currents and that the resistance of the cell membrane to low frequency current is primarily responsible for this difference. It is thus possible with this technique of alternating current spectroscopy to determine the average electrical conductivity of the cytoplasm of a red cell population. However this technique does not allow for the measurement of the internal conductivity of individual cells nor are means described to determine the hemoglobin concentration of individual red blood cells.

Pilwat and Zimmermann, "Determination of Intracellular Conductivity from Electrical Breakdown Measurements," *Biochimica et Biophysica Acta*, 820:305–314, 1985, described the determination of the average internal conductivity of cells within a flow cytometric aperture by the use of a high strength electrical field which causes breakdown of the cell membrane and thus allows current to pass through the cell. This technique then compares the electrical resistance for the disrupted cell population to measurements made at a lower field strength which does not disrupt the cells. With this technique, as with alternating current spectroscopy, an average measure for the internal conductivity of the cell population can be determined. While this technique can be made in a flow cytometric aperture, because it requires multiple passes of a population through the aperture rather than making all measurements on an individual cell, it can only produce an average measurement for the entire population. Again, the measurement of individual cell hemoglobin concentration cannot be made with this electrical technique.

There has been described two means to make measurements of individual cell hemoglobin concentration with a flow cytometer. U.S. Pat. No. 4,735,504 by Tycko (April 1988) describes the collection of scattered light over two angular regions for sphered red cells in a flow cytometric aperture to determine the volume and hemoglobin concentration of these cells. In addition, U.S. Pat. No. 5,194,909, also by Tycko (March 1993) describes the measurement of direct current resistance along with one angular region of light scatter on sphered red cells to simultaneously determine cell volume and hemoglobin concentration. Both techniques require the use of laser light sources, flow cells suitable for optical measurements fabricated of optically-pure materials, and photo-detectors and their associated electronics. The use of these optical techniques adds considerable cost and complexity to the measurement apparatus. Additionally, both techniques are very sensitive to the shape of the cell, and accurate measurements can only be determined when the cell, is perfectly spherical. Thus, measurement are not possible with red cells in their native shape.

Accordingly, there exists the need for a means to determine the hemoglobin concentration of individual red blood cells within a flow cytometric aperture that does not require the use of optical illumination and detection. As described herein, such an apparatus and method would have the ability to quickly and accurately determine individual cell hemoglobin concentration at a lower cost with a simpler instrument than is currently possible.

SUMMARY OF THE INVENTION

The present invention is directed to a method to determine the hemoglobin concentration of individual red blood cells. The method comprises the steps of entraining red blood cells of a blood sample into a stream of spaced apart, individual red blood cells in an electrolyte liquid; measuring the low frequency electrical resistance of the electrolytic liquid within an aperture, including measuring a change in the electrical resistance caused by the passing of each of the red blood cells of the stream through the aperture, and deriving a corresponding first pulse signal having an amplitude representative of the change in the electrical resistance caused by the passing of the red blood cell throughout the aperature measuring the radio frequency (RF) resistance of the electrolytic liquid within the aperture, including measuring a change in the radio frequency resistance caused by the passing of each of the red blood cells of the stream through the aperture, and deriving a corresponding second pulse signal having an amplitude representative of the change in the radio frequency resistance caused by the passing of the red blood cell throughout the aperture; determining a shape for each red blood cell; and calculating the hemoglobin concentration of each of the red blood cells of the stream from the corresponding first and second pulses and shape of the red blood cell. In addition, the method is applicable to apparatuses which have a non focus flow aperture and apparatus that employ a focus flow aperture.

The determination of the red blood cell shape can be made by different methods which include sphering the blood cells, direct measurement of the blood cells and selecting a constant value for the red blood cells.

The present inventions further relates to a method which further comprises determining the volume of the red blood cell using the measured change in the low frequency electrical resistance caused by the passing of each of the red blood cells of the stream through the aperture.

The method of the present invention enables the identification of subpopulations of red blood cells based upon the determination of red cell hemoglobin concentration.

In addition, the present invention relates to an apparatus for measuring the hemoglobin concentration of individual red blood cells. The apparatus contains a means for entraining red blood cells of a blood sample into a stream of spaced apart, individual red blood cells in an electrolyte liquid; a resistance measuring means for measuring the low frequency electrical resistance of the electrolytic liquid within an aperture, including measuring a change in the electrical resistance caused by the passing of each of the red blood cells of the stream through the aperture, and deriving a corresponding first pulse signal having an amplitude representative of the change in the electrical resistance caused by the passing of the red blood cell throughout the aperture; a radio frequency measuring means for measuring the radio frequency (RF) resistance of the electrolytic liquid within the aperture, including measuring a change in the radio frequency resistance caused by the passing of each of the red blood cells of the stream through the aperture, and deriving a corresponding second pulse signal having an amplitude representative of the change in the radio frequency resistance caused by the passing of the red blood cell throughout the aperture; a means for determining a shape for each red blood cell; and a means for calculating the hemoglobin concentration of each of the red blood cells of the stream from the corresponding first and second pulses and shape of the red blood cell.

In addition, the apparatus is directed to an instrument which can include a non focus flow aperture. Alternatively, the apparatus can employ a focus flow aperture.

Still further, the apparatus is directed to providing a determination of the shape of the red blood cells. In one embodiment of the apparatus, the apparatus contains a vessel (not shown) which is used to mix the red blood cells with a sphering agent to sphere the blood cells. In a second embodiment, the apparatus contains a means for the direct measurement of the blood cells. This means includes an imaging system to obtain an image of the red blood cell (not shown).

The present invention further relates to an apparatus which further comprises a means for determining the volume of the red blood cell using the measured change in the electrical resistance caused by the passing of each of the red blood cells of the stream through the aperture.

The present apparatus enables the identification of subpopulations of red blood cells based upon the determination of red cell volume and hemoglobin concentration.

BRIEF DESCRIPTION OF THE DRAWINGS

FIG. 7 is a hemoglobin concentration histogram of blood samples determined by the present invention. FIG. 7 (A) depicts a normal red cell population. FIG. 7 (B) shows a significant increase in red cells that are hypochromic red blood cells. FIG. 7 (C) shows a significant increase in red cells that are hyperchromic red blood cells.

DETAILED DESCRIPTION OF THE PREFERRED EMBODIMENTS

Figure 1:
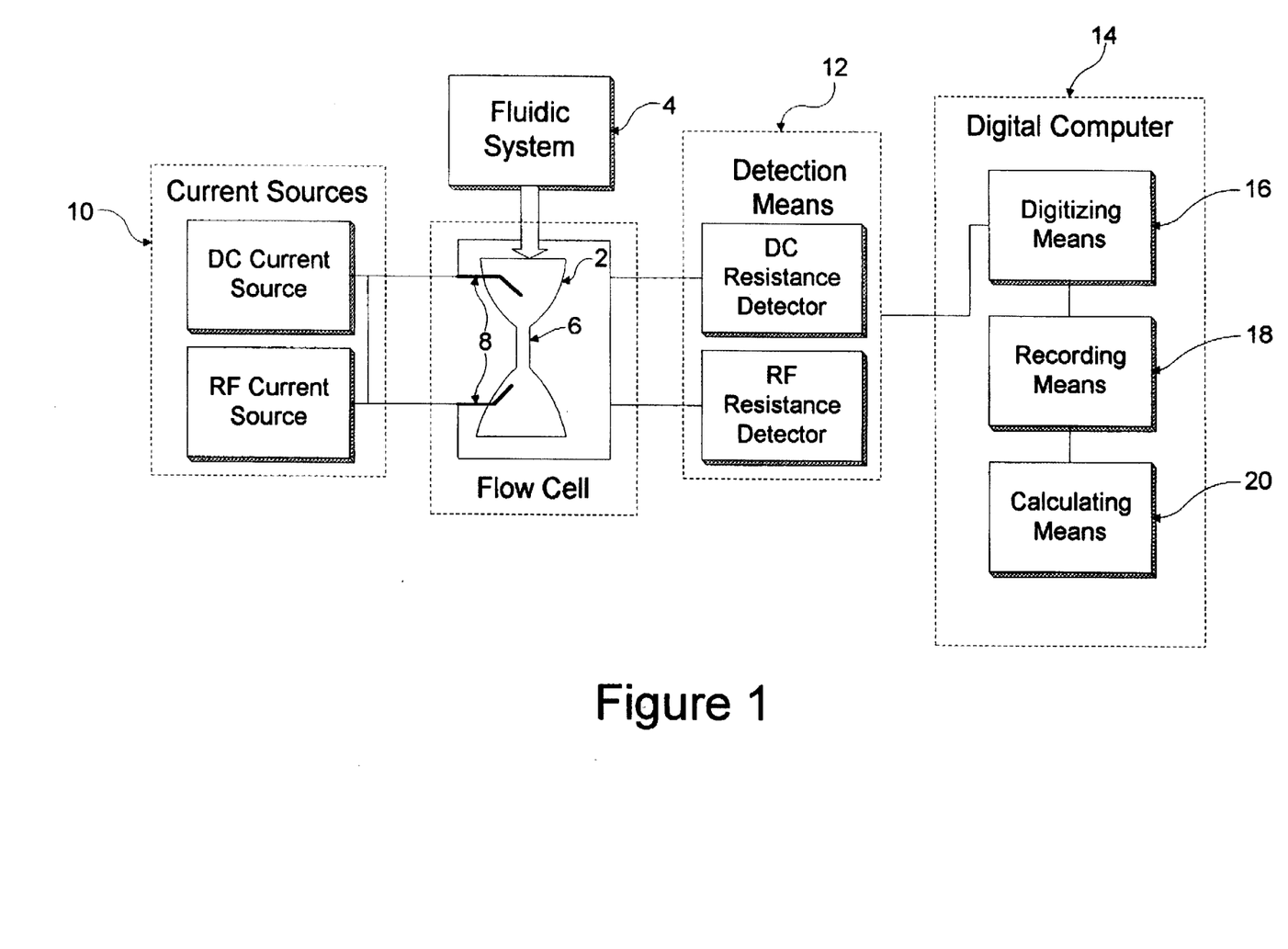
FIG. 1 is a schematic of an apparatus for use with the present invention.

As shown schematically in FIG. 1, the apparatus of this invention consists of a flow cell 2 attached to a fluidic system 4 that presents a diluted red blood cell sample to the flow cell. The flow cell 2 contains a measuring aperture 6, through which red blood cells flow substantially one at a time. Electrodes 8 are located on each side of the aperture. The electrodes are connected to electrical circuitry 10, capable of establishing a direct current field and a radio frequency alternating current electrical field across the aperture. Electrical circuitry 12 is also attached to the electrodes and measures changes in the DC and RF voltages that occur as red blood cells travel through the aperture. The output of this circuitry is connected to a computer 14 by digitizing means 16. The computer contains recording means 18 which records the magnitude of the change in DC voltage and RF voltage caused by each red blood cell passing through the aperture. The computer then performs an analysis using calculating means 20 to determine the hemoglobin concentration of the individual red cell that passed the aperture in accordance with the present disclosure. In addition, in a preferred embodiment, the volume of each red blood cell is calculated. Furthermore, the digital computer compiles statistical measurements for the red cell population, including the mean, standard deviation and coefficient of variation of cellular hemoglobin concentration and volume.

To determine the hemoglobin concentration of individual red blood cells an aliquot of red blood cells is diluted with a isotonic solution of known conductivity. The dilution should be in a ratio to ensure that the cells can flow through the aperture substantially one at a time. Typical dilutions are known to those skilled in art for the intended purpose. Usually the dilutions are greater than 1 to 1. For instruments which use a focus flow aperture system, the dilution of the red blood cells to the electrolyte is approximately 1 to 2,500. For instruments which use a non focus flow aperture system, the dilution of the red blood cells to the electrolyte is approximately 1 to 5,000.

The range of conductivity of the isotonic solution has not been shown to be significant. A broad range of conductivity has been shown to be useful in this invention. The isotonic solution is typically a buffered salt solution of sodium chloride having a neutral pH. An example of a suitable isotonic solution is an isotonic phosphate-buffered saline solution of pH 7.4 and osmolarity of approximately 290 mOsm.

The hemoglobin concentration of the cell is obtain from analyzing the DC and RF resistance of the red blood cell measured as the cell flows through a measurement aperture. The electrical resistance cause by a particle or cell suspended within an electrically conductive fluid as it flows through a measurement aperture is determined by the volume of the particle or cell, its shape and orientation, and the electrical conductivity of that particle or cell relative to the suspending fluid for that particular frequency of electrical current. The sum effect of the shape, orientation and conductivity of the cell or particle is referred to as a "shape factor".

For cells or particles which are ellipsoids of revolution, with their long axis oriented parallel to the electrical field, the shape factor, $f_s$, is equal to:

$$f_s = \frac{2[1-(\sigma_c/\sigma_e)]}{2 + \left[ 2 + \frac{2m^2}{1-m^2} - \frac{m \cdot \ln(z)}{(m^2-1)^{3/2}} \right] ((\sigma_c/\sigma_e)-1)} \quad (1)$$

where $\sigma_c$ is the conductivity of the cell at a particular frequency, $\sigma_3$ is the conductivity of the external solution at that frequency, m is the ratio of the of the ellipsoid's length (major axis) to its width (minor axis), and z is a function of m defined as:

$$z = \frac{m - (m^2 - 1)^{1/2}}{m + (m^2 - 1)^{1/2}} \quad (2)$$

The ratio of the conductivity of the cell to the conductivity of the external medium, $\sigma_c/\sigma_e$, as it appears in Equation 1, is referred to as the relative conductivity.

For a low frequency measurement (including DC), a blood cell appears as an insulator to the electric field due to the electrical non-conductivity of its membrane at this frequency. In this situation, the cell's conductivity $\sigma_c$ is very small relative to the suspending solution conductivity, $\sigma_e$ and thus the ratio $\sigma_c/\sigma_e$ is essentially 0. Applying this simplification to Equation 1, the shape factor of a blood cell for a direct current, $f_{s,DC}$ can be described as:

$$f_{s,DC} = \frac{2}{2 - \left[2 + \frac{2m^2}{1-m^2} - \frac{m \cdot \ln(z)}{(m^2-1)^{3/2}}\right]} \quad (3)$$

As the frequency of the current increases, the dielectric or insulating capacity of the cell membrane is lost. At radio frequencies (RF), the membrane appears nearly invisible to the electric field. Then, the conductivity of the cell is determined by the conductivity of its interior. For the red blood cell, the interior normally contains only a solution of hemoglobin and does not contain a nucleus or other internal structures. Therefore, the conductivity of the hemoglobin solution that makes up the cell's cytoplasm is totally responsible for the determining the conductivity of the cell to RF currents. For red cells, the electrical conductivity of the cytoplasm is of the same order of magnitude as the conductivity of external buffered salt solution in which the cells are suspended. Thus, for the RF measurement, the simplification applied to Equation 1 for the DC measurement cannot be applied, and the shape factor $f_{s,RF}$, is described by the full terms of Equation 1.

The electrical resistance (R) of a particle in the field, such as a DC or RF resistance, is equal to the volume of the particle (V) times the shape factor times a system constant (k), or $$R = V \cdot f_s \cdot k \quad (4)$$

As previously described, the opacity is defined as the RF resistance divided by the DC resistance or $$\text{Opacity} = \frac{R_{RF}}{R_{DC}} = \frac{V_{RF} \cdot f_{s,RF} \cdot k_{RF}}{V_{DC} \cdot f_{s,DC} \cdot k_{DC}} \quad (5)$$

Since the volume of the cell is the same for both the DC and RF measurements, and in that the system constants $k_{RF}$ and $k_{DC}$ can be set to be equal by adjusting gain controls or other means, the opacity becomes only the ratio of the shape factors, or $$\text{Opacity} = \frac{f_{s,RF}}{f_{s,DC}} \quad (6)$$

As previously stated, $f_{s,DC}$ is described by Equation 3 and $f_{s,RF}$ is described by Equation 1. Therefore, the opacity of a cell is described as:

$$\text{Opacity} = \frac{2 + \left[2 + \frac{2m^2}{1-m^2} - \frac{m \cdot \ln(z)}{(m^2-1)^{3/2}}\right]((\sigma_c/\sigma_e) - 1)}{2 - \left[2 + \frac{2m^2}{1-m^2} - \frac{m \cdot \ln(z)}{(m^2-1)^{3/2}}\right]} \quad (7)$$

As can be seen in this equation, the opacity of a cell is dependent only upon the shape of the cell, as described by the parameter "m", and upon the ratio of the conductivity of the interior of the cell to the conductivity of the external medium ($\sigma_c/\sigma_e$).

To determine the hemoglobin concentration in a blood cell by opacity, one must know the relationship between the hemoglobin concentration of the red cell's cytoplasm and the electrical conductivity of that cytoplasmic solution. Due to the difficulty of measuring this relationship within the small scale of a red blood cell itself, an experimental model was developed to determine this relationship. A known quantity of a buffered salt was added to a known amount of water to create a solution of known electrical conductivity. Then a specific amount of hemoglobin was added to the salt solution resulting in a first hemoglobin concentration. The conductivity of this first hemoglobin solution was measured. Next an additional amount of hemoglobin was added to the first hemoglobin solution resulting in a second hemoglobin concentration. The conductivity of this second solution was measured. This process was repeated over a broad range of hemoglobin concentrations. The dependence of the conductivity of the hemoglobin solutions to the initial salt concentration of the buffered salt solution was found by repeating this experiment at several initial concentrations of the buffered salt. The results of this series of experiments are shown in FIG. 2.

Figure 2:
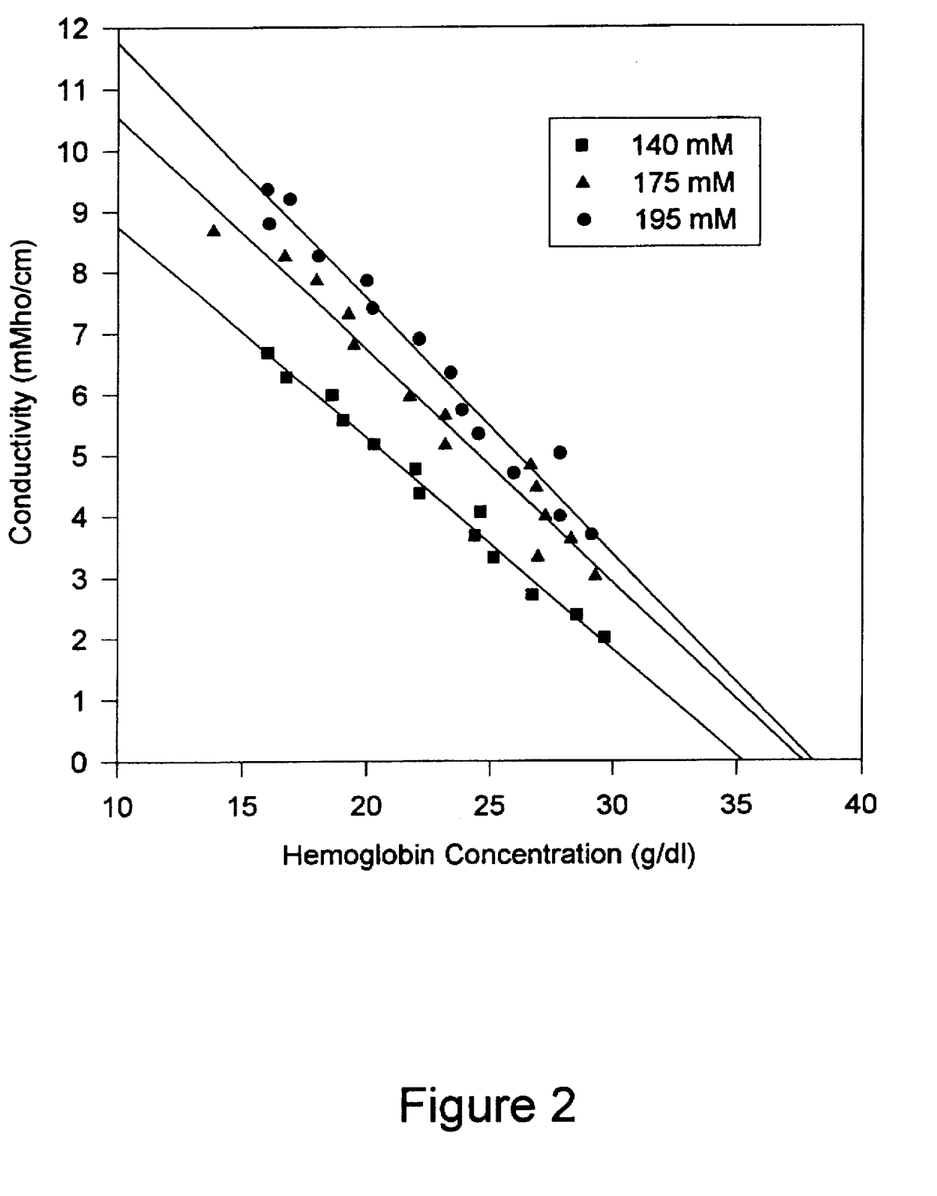
FIG. 2 is a diagram of the relationship between the initial ionic content of a buffered salt solution, the solution's concentration of hemoglobin, and the electrical conductivity of the resulting mixture.
Figure 3:
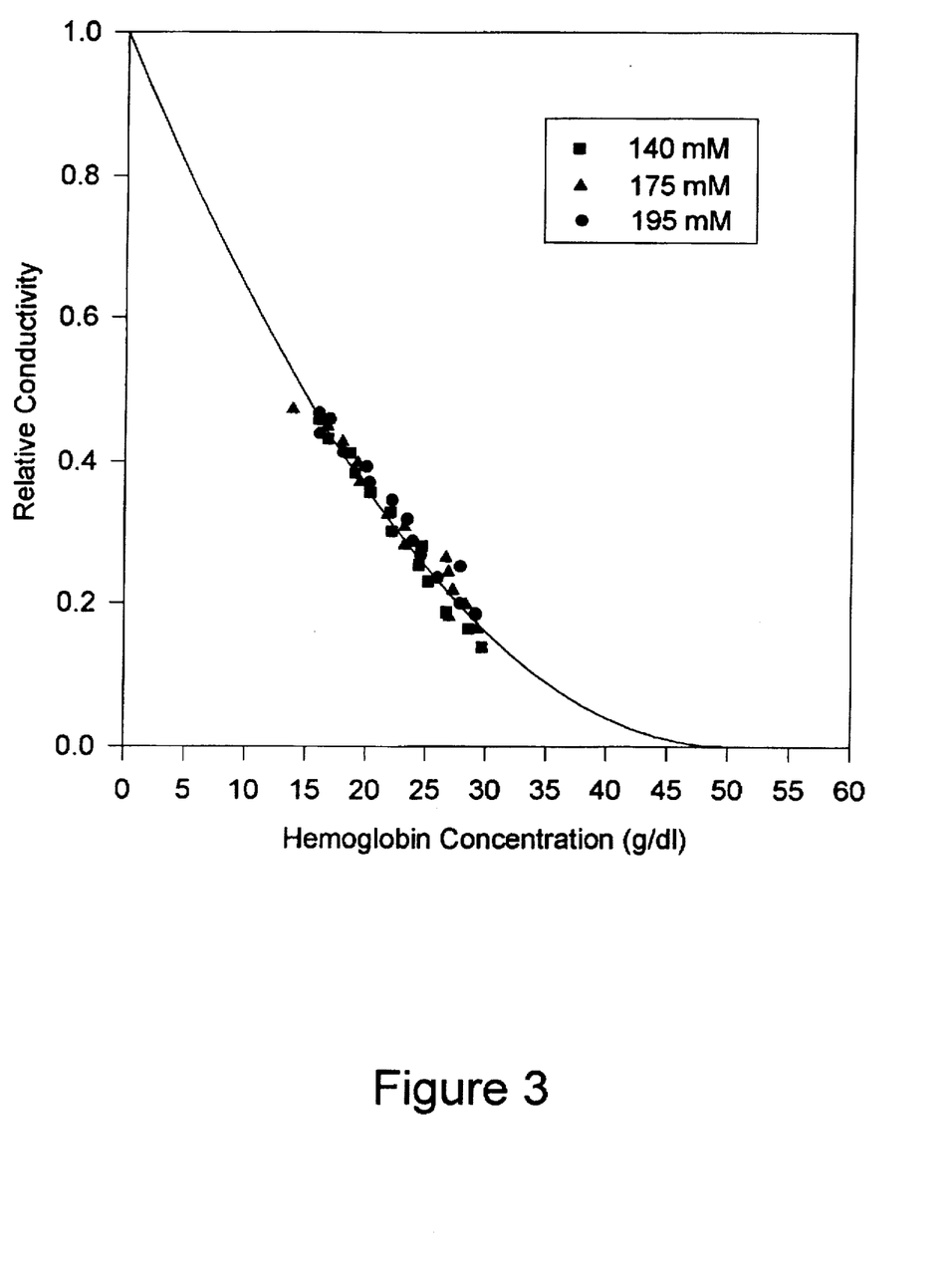
FIG. 3 is a diagram of the relationship between the concentration of hemoglobin in a buffered salt solution and the electrical conductivity of the solution relative to the buffered salt solution without hemoglobin present.

The results of FIG. 2 can be simplified by dividing the conductivity of each hemoglobin solution by the conductivity of the initial salt solution from which the hemoglobin solution is derived. This scaled conductivity can also be referred to as a relative conductivity. The result of this scaling is seen in FIG. 3, which reveals that a single curve describes the relative conductivity of hemoglobin solutions, independent of the initial salt concentration. This result is described mathematically by regressing the data shown in this figure to an equation of the following general form:

$$\text{Relative\_Conductivity} = (1 - x \cdot Hb)^y \quad (8)$$

Here, Hb is the hemoglobin concentration. This regression gives the following specific equation:

$$\text{Relative\_Conductivity} = (1 - 0.016 \cdot Hb)^{1.49} \quad (9)$$

In the method to determine the hemoglobin concentration of individual red cells by the measurement of opacity, as described in this disclosure, the cells are diluted into a large volume of buffered salt solution. Whereas the membrane of the red cell allows both water flux and ion transport through it, the red cell will respond to dilution in an external solution of a specific ionic concentration by adjusting its internal solution to an ion concentration approximately equal to the external solution ion concentration. Thus the relative conductivity, as determined in the experiments described above and described in Equation 9, is equal to the relative conductivity as measured by opacity in the method described herein and described in Equation 7. Therefore, by combining Equations 7 and 9, the relationship between hemoglobin concentration and opacity is determined. This result is described in Equation 10 as:

$$\text{Opacity} = \frac{2[1 - (1 - .016 \cdot Hb)^{1.49}]}{2 + \left[2 + \frac{2m^2}{1-m^2} - \frac{m \cdot \ln(z)}{(m^2-1)^{3/2}}\right]((1 - .016 \cdot Hb)^{1.49} - 1)} \quad (10)$$

$$\frac{}{2 - \left[2 + \frac{2m^2}{1-m^2} - \frac{m \cdot \ln(z)}{(m^2-1)^{3/2}}\right]}$$

Figure 4:
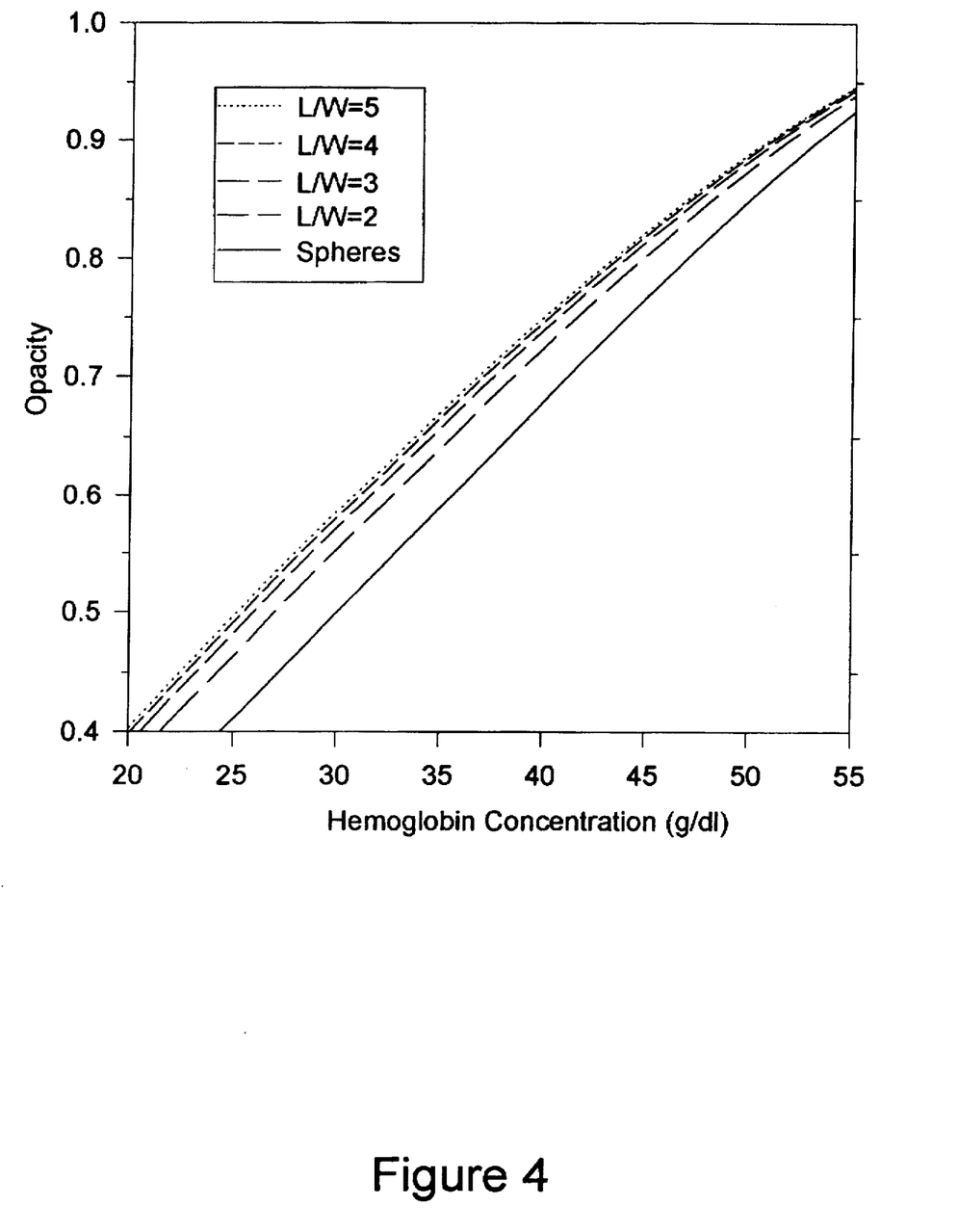
FIG. 4 is a diagram which depicts the dependency upon the shape of the cell of the relationship between the hemoglobin concentration of a red blood cell and the opacity measurement of the cell.

This relationship between hemoglobin concentration and opacity is plotted in FIG. 4 for a range of the cell shape parameter "m". As seen in this figure, there can be a substantial difference in the opacity measurement for a given hemoglobin concentration due to variations in the shape of the red cell.

Thus it is necessary to account for the shape of the cell in order to accurately determine the hemoglobin concentration from the opacity measurement. There are several alternative means to account for the cell shape.

One alternative means would be to isovolumetrically sphere the red cells. In a optional embodiment the sphered cells can be stabilized with known cell fixative reagent. The means to isovolumetrically sphere red cells are well known to those skilled in the art. Typically a sphering reagent can be used to transform the red blood cells from their normal biconcave disk shape into spheres by reducing the surface area of the cell membrane to be as small as possible. When using a sphering agent, preferably the red cell volume should remain nearly constant and not change due to the use of the sphering agent. When using sphered red blood cells, the shape parameter "m" would be equal to 1 for all cells, and the hemoglobin concentration can be determined by Equation 10 or FIG. 4 accordingly.

A second alternative means to account for the cell shape would be to measure the shape of each cell. Several methods to do so are known to those skilled in the art of cytometry. Methods to directly measure the shape of each cell would include a direct imaging method or a slit scanning method which is taught by Groves et al.

A third alternative means to account for the cell shape would be to assume a shape of the cell. This method is possible because a normal population of red cells has a consistent and known shape and deformability. While using this method would be the simplest to implement, it does have the potential for inaccuracy, particularly for samples of red cells that do not conform to the normal behavior.

Experiment verification of the above analysis has been performed with both a model system and with patient blood samples. The model system utilizes the technique of Clark et al., "Study on the Dehydrating Effect of the Red Cell Na*/K*-Pump in Nystatin-treated Cells with Varying Na* and Water Contents," Biochimica et Biophysica Acta, 646:422–432, 1981, to produce populations of red cells with narrowly defined hemoglobin concentrations. With this technique, it is possible to produce populations with hemoglobin concentrations from approximately 20 g/dl to 50 g/dl. This range exceeds the range of hemoglobin concentrations seen in both normal and abnormal people.

Figure 5:
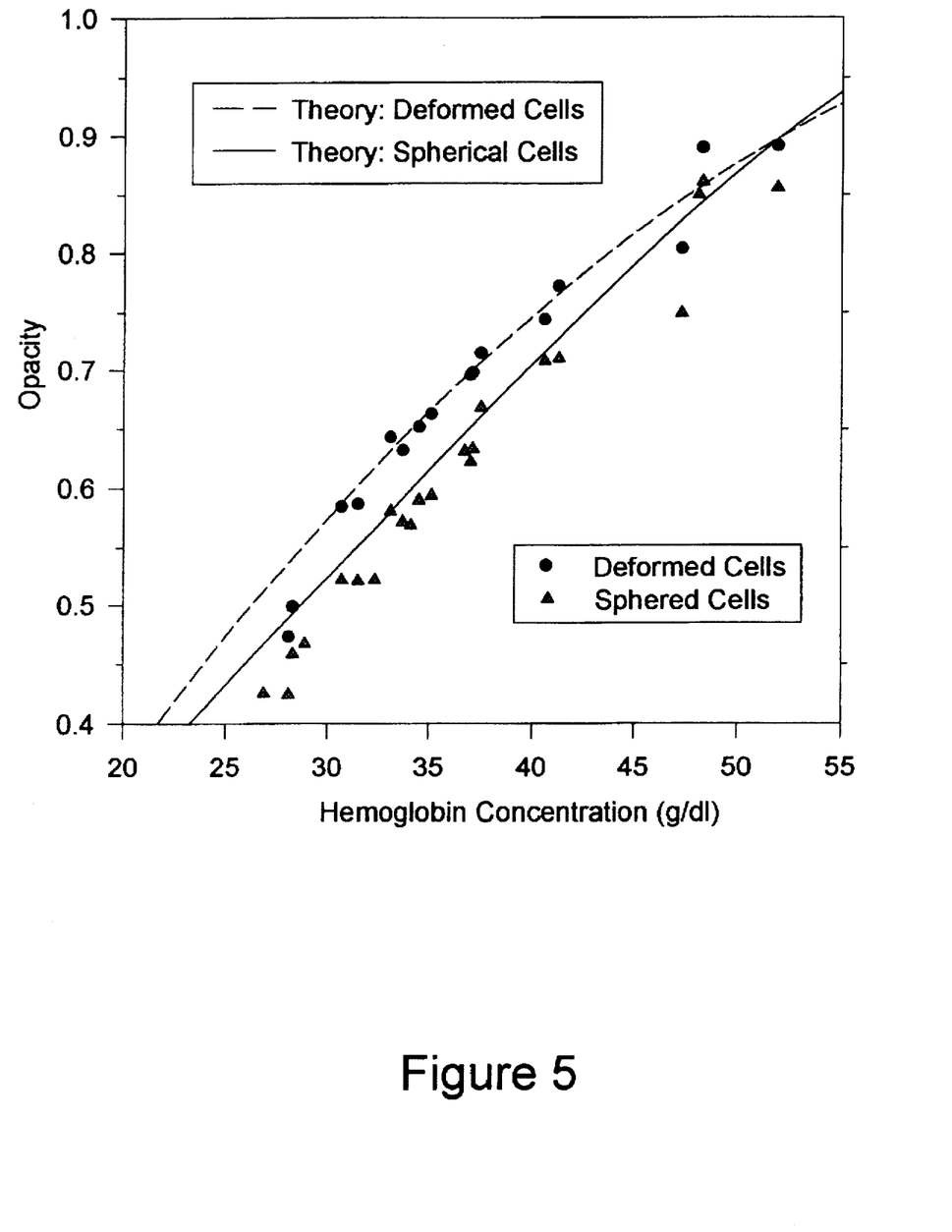
FIG. 5 is diagram which depicts opacities of sphered and deformable red cells as a function of hemoglobin concentrations. The curves represent the theoretical projections expected based upon the analysis developed in this application.

FIG. 5 shows results with cells treated with this technique to create samples of cells with specific concentration of hemoglobin. Cells are measured both after sphering and in their normal state. The solid lines in this figure represent the predicted measurement of opacity for a given hemoglobin concentration, as described by this disclosure, both for cells fixed in the spherical shape and for cells retaining normal deformability. Close agreement is seen for both populations of cells. It should be noted that the normal deformability of a cell varies with hemoglobin concentration, among other factors, and that cells with high hemoglobin concentration behave in a manner similar to the sphered cells.

Figure 6:
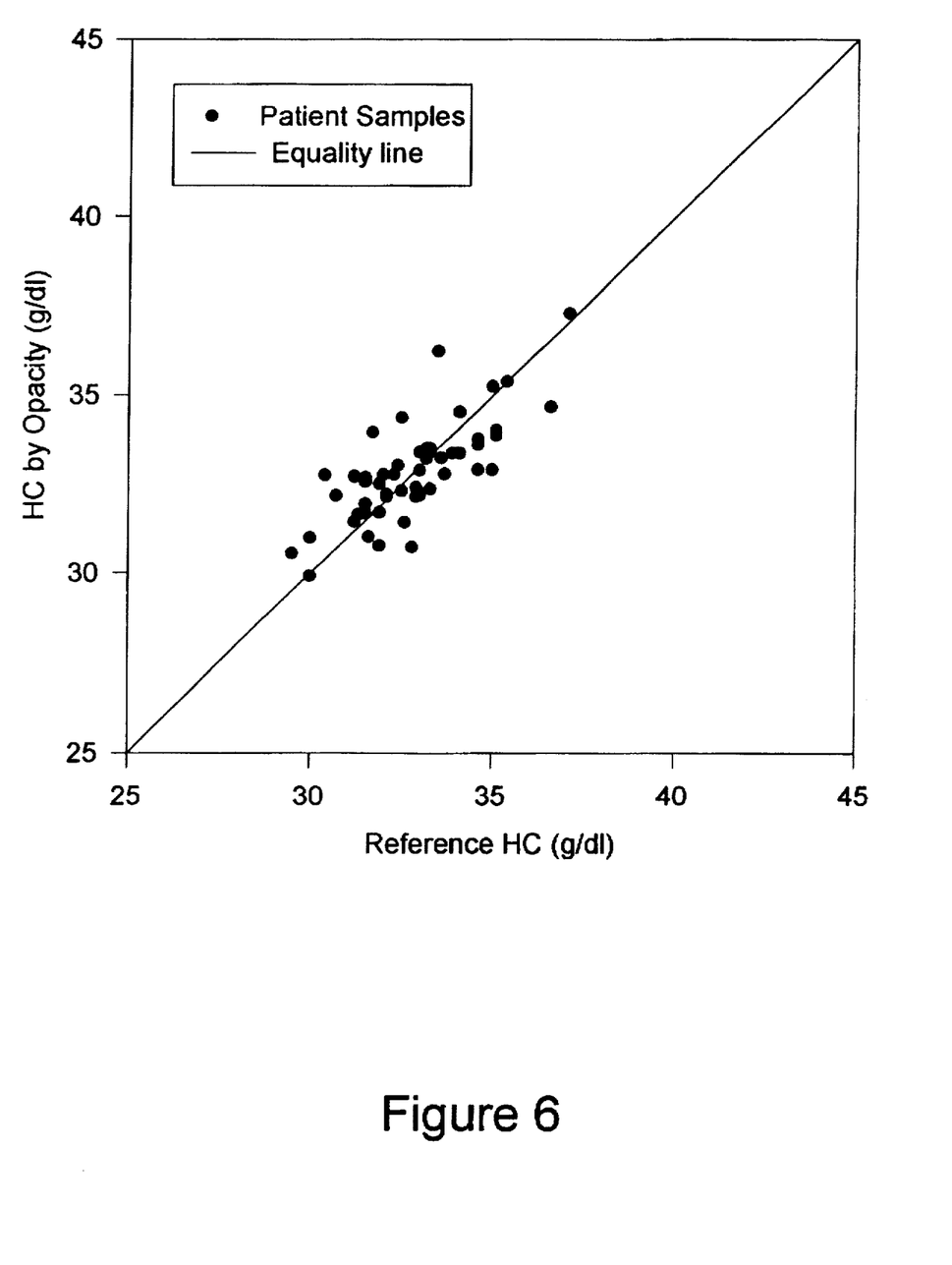
FIG. 6 is a comparison of hemoglobin concentration determined by the method of this invention versus a reference method for 54 patient samples.

The results of the hemoglobin concentration measurement by the opacity method described herein for a group of 54 patient samples measured after fixing the cells as spheres is seen in FIG. 6. The hemoglobin measurement as determined by the opacity method is compared to hemoglobin as measured by the reference colorimetric method. The line of equivalence between these two measurements is also plotted. For this data set, the standard deviation between the hemoglobin concentration as measured by the opacity technique described herein, and hemoglobin concentration as determined by the reference colorimetric method, is 1.09 g/dl.

Figure 7A:
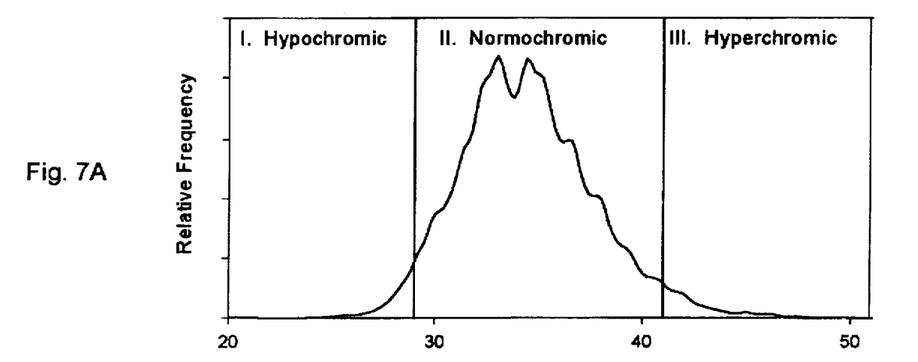
Figure 7B:
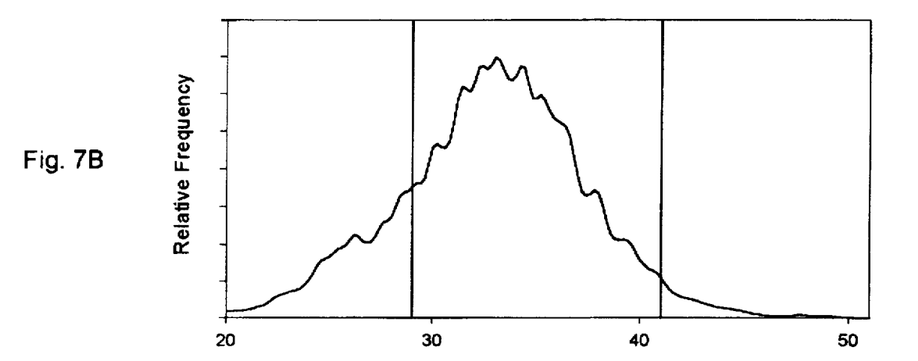
Figure 7C:
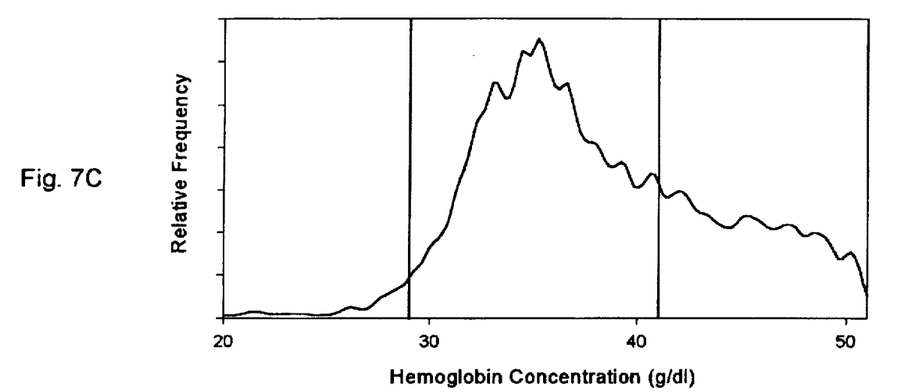

The ability of this invention to detect a hemoglobin concentration distribution is shown in FIG. 7. FIG. 7 (A) shows a normal red blood cell population having a majority of cells with a hemoglobin concentration between 29 g/dl and 41 g/dl. This red blood cell subpopulation is described as being normochromic. FIG. 7 (B) is a hemoglobin distribution from a patient which exhibited a significant hypochromic subpopulation of red blood cells. FIG. 7 (C) is a hemoglobin distribution from a different patient which exhibited a significant hyperchromic subpopulation of red blood cells. The method of Example 3 was employed to obtain these determinations.

It should be appreciated that the following Examples provide methods and formulations for the determination of hemoglobin concentration of individual red blood cells which are only illustrative. Other reagents and/or techniques can be employed, in accordance with this disclosure.

EXAMPLE 1

A sample of 2 μl of whole blood is diluted into 5 ml of 10 mM sodium phosphate buffer, pH of 7.4, containing 140 mM sodium chloride adjusted to 290 mOsm. The sample is aspirated into a hematology analyzer with a flow cell employing hydrodynamic focusing and containing a cylindrical measurement aperture of the dimensions of approximately 50 microns in diameter by 70 microns long. The flow cell contains two electrodes, one on each side of the aperture, which are connect to appropriate electronic circuitry to allow for the measurement of direct current (DC) resistance and radio frequency (RF) resistance at a frequency of 23 MHz across the aperture. The diluted sample of blood, typically containing greater than 99% red cells is caused to flow through the measurement aperture essentially one cell at a time, as determined by the dilution ratio of the blood sample and the volume of the aperture. The hydrodynamic focusing of the fluid stream containing the sample of cells with a second fluid stream causes an additional dilution by a factor of approximately 4. The velocity of flow is set to be approximately 5 meters per second within the measurement aperture. The red cells deform in response to the fluidic forces exerted upon them during flow. Measurements of the DC and RF resistance are recorded for each of approximately 32,000 cells. The hemoglobin concentration of each cell is determined from the opacity measurement as described herein with the assumption that each cell assumes a shape with a length to width ratio of 4 to 1 during the measurement. The mean of the hemoglobin concentration is computed from the individual hemoglobin concentration determinations, as well as the statistical measures of the standard deviation and coefficient of variation of the population. A histogram of the hemoglobin concentration of the population is also produced, and hypochromic and hyperchromic populations are identified.

EXAMPLE 2

A sample of 2 µl of whole blood is diluted into 5 ml of 10 mM sodium phosphate buffer, pH of 7.4, containing 140 mM sodium chloride adjusted to 290 mOsm. The sample is aspirated into a hematology analyzer with a flow cell employing hydrodynamic focusing and containing a rectangular measurement aperture of the dimensions of approximately 50 microns by 50 microns in cross section and 70 microns long. The flow cell contains two electrodes, one on each side of the aperture, which are connect to appropriate electronic circuitry to allow for the measurement of direct current (DC) resistance and radio frequency (RF) resistance at a frequency of 23 MHz across the aperture. An imaging system is also fitted to the aperture, to allow images of individual cells to be recorded as they flow through the aperture. The diluted sample of blood, typically containing greater than 99% red cells is caused to flow through the measurement aperture essentially one cell at a time, as determined by the dilution ratio of the blood sample and the volume of the aperture. The hydrodynamic focusing of the fluid stream containing the sample of cells with a second fluid stream causes an additional dilution by a factor of approximately 4. The velocity of the flow is set to be approximately 5 meters per second within the measurement aperture. The red cells deform in response to the fluidic forces exerted upon them during flow. Measurements of the DC and RF resistance are recorded for each of approximately 32,000 cells. An image of the shape of each cell while in the measurement aperture is obtained along with the DC and RF measurements. The shape of each cell, as described by the ratio of its length to width, is obtained from the image. The hemoglobin concentration of each cell is determined from the opacity measurement and from the shape measurement by the analysis described herein. The mean of the hemoglobin concentration is computed from the individual hemoglobin concentration determinations, as well as the statistical measures of the standard deviation and coefficient of variation of the population. A histogram of the hemoglobin concentration of the population is also produced, and hypochromic and hyperchromic populations are identified.

EXAMPLE 3

A sample of 2 µl of whole blood is diluted into 5 ml of 7.0 mM sodium citrate buffer, pH 7.4, containing 74 mM KCl, 71 mM NaCl, 100 µg/dl of the detergent n-dodecyl-n, n-dimethyl-3-ammonio-1-propane sulfonate (DDAPS) and 0.1% gluteraldehyde at 290 mOsm. Dilution of the red cells into the solution results in the iso-volumetric sphering of each cell and the fixation of the cell to prevent deformation during flow. The sample is aspirated into a hematology analyzer with a flow cell employing hydrodynamic focusing and containing a cylindrical measurement aperture of the dimensions of approximately 50 microns in diameter by 70 microns long. The flow cell contains two electrodes, one on each side of the aperture, which are connect to appropriate electronic circuitry to allow for the measurement of direct current (DC) resistance and radio frequency (RF) resistance at a frequency of 23 MHz across the aperture. The diluted sample of blood, typically containing greater than 99% red cells is caused to flow through the measurement aperture essentially one cell at a time, as determined by the dilution ratio of the blood sample and the volume of the aperture. The hydrodynamic focusing of the fluid stream containing the sample of cells with a second fluid stream causes an additional dilution by a factor of approximately 4. Measurements of the DC and RF resistance are recorded for each of approximately 32,000 cells. The hemoglobin concentration of each cell is determined from the opacity measurement as described herein with the knowledge that each cell has a spherical shape during the measurement. The mean of the hemoglobin concentration is computed from the individual hemoglobin concentration determinations, as well as the statistical measures of the standard deviation and coefficient of variation of the population. A histogram of the hemoglobin concentration of the population is also produced, and hypochromic and hyperchromic populations are identified.

EXAMPLE 4

A sample of 1 µl of whole blood is diluted into 10 ml of 7.0 mM sodium citrate buffer, pH 7.4, containing 74 mM KCl, 71 mM NaCl, 100 µg/dl of the detergent n-dodecyl-n, n-dimethyl-3-ammonia-1-1-propane sulfonate (DDAPS) and 0.1% gluteraldehyde at 290 mOsm. The dilution results in the iso-volumetric sphering of each cell and the fixation of the cell to prevent deformation during flow. The sample is aspirated into a hematology analyzer with a flow cell that does not employ hydrodynamic focusing and containing a cylindrical measurement aperture of the dimensions of approximately 50 microns in diameter by 70 microns long. The flow cell contains two electrodes, one on each side of the aperture, which are connect to appropriate electronic circuitry to allow for the measurement of direct current (DC) resistance and radio frequency (RF) resistance at a frequency of 23 MHz across the aperture. The diluted sample of blood, typically containing greater than 99% red cells is caused to flow through the measurement aperture essentially one cell at a time, as determined by the dilution ratio of the blood sample and the volume of the aperture. Measurements of the DC and RF resistance are recorded for each of approximately 32,000 cells. The hemoglobin concentration of each cell is determined from the opacity measurement as described herein with the knowledge that each cell has a spherical shape during the measurement. The mean of the hemoglobin concentration is computed from the individual hemoglobin concentration determinations, as well as the statistical measures of the standard deviation and coefficient of variation of the population. A histogram of the hemoglobin concentration of the population is also produced, and hypochromic and hyperchromic populations are identified.

While in the foregoing specification, a detailed description of the invention has been set down for the purpose of illustration, many variations in the details herein give may be made by those skilled in the art without departing from the spirit and scope of the invention.

We claim:

1. A method to determine the hemoglobin concentration of individual red blood cells comprising the steps of a. entraining red blood cells of a blood sample into a stream of spaced apart, individual red blood cells in an electrolytic liquid, b. measuring low frequency electrical resistance of the electrolytic liquid within an aperture, including measuring a change in the electrical resistance caused by the passing of each of the red blood cells of the stream through the aperture, and deriving a corresponding first pulse signal for each red blood cell having an amplitude representative of the change in the electrical resistance caused by the passing of each red blood cell through the aperture, c. measuring radio frequency (RF) resistance of the electrolytic liquid within the aperture, including measuring a change in the radio frequency resistance caused by the passing of each of the red blood cells of the stream through the aperture, and deriving a corresponding second pulse signal for each red blood cell having an amplitude representative of the change in the radio frequency resistance caused by the passing of each red blood cell through the aperture, d. determining a shape for each red blood cell, and e. calculating the hemoglobin concentration of each of the red blood cells of the stream from a ratio of the corresponding second pulse signal to first pulse signal and the shape of the red blood cells.

2. The method of claim 1, wherein the determining of the shape is made by mixing the red blood cells with a chemical reagent which results in the red blood cells being sphered.

3. The method of claim 1, wherein the determining of the shape is made by direct measurement of the red blood cells.

4. The method of claim 3, wherein the direct measurement of the red blood cells is made by optically imaging the red blood cells.

5. The method of claim 1, wherein the determining of the shape is made by assuming a constant shape for the red blood cells.

6. The method of claim 1, wherein the aperture comprises a non-focus flow aperture.

7. The method of claim 1, wherein the aperture comprises a focus flow aperture and wherein the red blood cells are sheathed in said electrolytic liquid.

8. The method of claim 1 which further comprises determining the volume of each red blood cell.

9. The method of claim 8, which further comprises identification of subpopulations of red blood cells based upon the determination of each red blood cell hemoglobin concentration.

10. The method of claim 9, wherein the subpopulations of red blood cells comprise normochromic, hyperchromic and hypochromic red blood cells.

11. An apparatus for measuring the hemoglobin concentration of individual red blood cells comprising:

a. means for entraining red blood cells of a blood sample into a stream of spaced apart, individual red blood cells in an electrolyte liquid, b. resistance measuring means for measuring low frequency electrical resistance of the electrolytic liquid within an aperture, including measuring a change in the electrical resistance caused by the passing of each of the red blood cells of the stream through the aperture, and deriving a corresponding first pulse signal for each red blood cell having an amplitude representative of the change in the electrical resistance caused by the passing of each red blood cell through the aperture, c. radio frequency measuring means for measuring radio frequency (RF) resistance of the electrolytic liquid within the aperture, including measuring a change in the radio frequency resistance caused by the passing of each of the red blood cells of the stream through the aperture, and a corresponding second pulse signal for each red blood cell having an amplitude representative of the change in the radio frequency resistance caused by the passing of each red blood cell through the aperture, d. means for determining a shape for each red blood cell, and e. means for calculating the hemoglobin concentration of each of the red blood cells of the stream from a ratio of the corresponding second pulse signal to first pulse signal and the shape of the red blood cells.

12. The apparatus of claim 11, wherein the means for determining the shape comprises means for mixing the red blood cells with a chemical reagent which results in the red blood cells being sphered.

13. The apparatus of claim 11, wherein the means for determining the shape comprises means for making a direct measurement of the red blood cells.

14. The apparatus of claim 13, wherein the direct measurement of the red blood cells is made by optically imaging the red blood cells.

15. The apparatus of claim 11, wherein the means for determining the shape comprises means for assuming a constant shape for the red blood cells.

16. The apparatus of claim 11, wherein the aperture comprises a non-focus flow aperture.

17. The apparatus of claim 11, wherein the aperture comprises a focus flow aperture and wherein the red blood cells are sheathed with said electrolytic liquid.

18. The apparatus of claim 11 which further comprises a means for determining the volume of each blood cell.

19. The apparatus of claim 18, which further comprises a means for identification of subpopulations of red blood cells based upon the determination of each red blood cell hemoglobin concentration.

20. The apparatus of claim 19, wherein the means for identification of subpopulations of red blood cells enables the determination of normochromic, hyperchromic and hypochromic red blood cells.

* * * * *